(12) United States Patent
Oliveira et al.

(10) Patent No.: US 11,819,262 B2
(45) Date of Patent: Nov. 21, 2023

(54) DEVICE, SYSTEM AND METHOD FOR TREATING SWOLLEN VASCULAR STRUCTURES

(71) Applicant: BE MEDICAL TECHNOLOGY CORP, Coral Springs, FL (US)

(72) Inventors: Enio Chaves De Oliveira, Goiânia (BR); Mauro Bafutto, Goiânia (BR)

(73) Assignee: BE MEDICAL TECHNOLOGY CORP, Coral Springs, FL (US)

(*) Notice: Subject to any disclaimer, the term of this patent is extended or adjusted under 35 U.S.C. 154(b) by 808 days.

(21) Appl. No.: 16/461,247

(22) PCT Filed: Mar. 19, 2018

(86) PCT No.: PCT/BR2018/050074
§ 371 (c)(1),
(2) Date: May 15, 2019

(87) PCT Pub. No.: WO2018/165731
PCT Pub. Date: Sep. 20, 2018

(65) Prior Publication Data
US 2020/0085494 A1    Mar. 19, 2020

Related U.S. Application Data

(60) Provisional application No. 62/472,737, filed on Mar. 17, 2017.

(51) Int. Cl.
*A61B 18/14* (2006.01)
*A61B 8/08* (2006.01)
(Continued)

(52) U.S. Cl.
CPC ........ *A61B 18/1485* (2013.01); *A61B 8/0891* (2013.01); *A61B 8/12* (2013.01);
(Continued)

(58) Field of Classification Search
CPC .......... A61B 2018/005; A61B 18/1485; A61B 8/0891; A61B 2018/143; A61B 2017/3245
See application file for complete search history.

(56) References Cited

U.S. PATENT DOCUMENTS 4,926,380 A * 5/1990 Harada ............... G01S 7/52023
367/7
5,385,544 A * 1/1995 Edwards ............ A61B 18/1485
604/164.08
(Continued)

FOREIGN PATENT DOCUMENTS

BR          0618702        12/2012
CN       203749448 U  *    8/2014
(Continued)

OTHER PUBLICATIONS

Bor ["Role of ultrasound in colorectal diseases", World J Gastroenterol Nov. 21, 2016; 22(43): 9477-9487]. (Year: 2016).*

*Primary Examiner* — Oommen Jacob
(74) *Attorney, Agent, or Firm* — K&L Gates LLP

(57) ABSTRACT

The present invention describes device, method and system for providing treatment for swollen vascular structures located in a body canal of a patient. The device, method and system described in here provide an easy and, practical treatment and with minimal or without disturb to the patient, including RF emission driven directly and specifically over such vascular structure, and by means of ultrasound technology verify the position of the vascular structure and whether it is closed before, during and after the RF application. The present invention is situated in the field of medical science, more precisely in treatment of vascular structures, and medical devices.

9 Claims, 11 Drawing Sheets

(51) Int. Cl.
*A61B 8/12* (2006.01)
*A61B 18/00* (2006.01)

(52) U.S. Cl.
CPC . *A61B 2018/005* (2013.01); *A61B 2018/0063* (2013.01); *A61B 2018/00404* (2013.01); *A61B 2018/00642* (2013.01)

(56) References Cited

U.S. PATENT DOCUMENTS

| | | | | |
|---|---|---|---|---|
| 6,077,257 | A * | 6/2000 | Edwards | A61B 18/12 607/101 |
| 6,296,638 | B1 * | 10/2001 | Davison | A61B 18/1482 604/35 |
| 7,160,294 | B2 | 1/2007 | Croft | |
| 8,277,376 | B2 | 10/2012 | Bastia | |
| 8,439,935 | B2 | 5/2013 | Bastia | |
| 9,192,427 | B2 * | 11/2015 | Johnson | A61B 18/1402 |
| 2002/0107515 | A1 * | 8/2002 | Edwards | A61B 18/1492 606/41 |
| 2005/0010203 | A1 * | 1/2005 | Edwards | A61B 18/18 607/101 |
| 2011/0257646 | A1 * | 10/2011 | Utley | A61B 18/149 606/33 |
| 2012/0004546 | A1 | 1/2012 | Neuberger et al. | |
| 2012/0059394 | A1 * | 3/2012 | Brenner | A61B 17/122 606/142 |
| 2015/0057646 | A1 * | 2/2015 | Aljuri | A61B 90/37 606/10 |
| 2016/0106435 | A1 * | 4/2016 | Brenner | A61B 1/31 600/439 |
| 2017/0049500 | A1 | 2/2017 | Shikhman et al. | |
| 2020/0085494 | A1 * | 3/2020 | Oliveira | A61B 18/1485 |

FOREIGN PATENT DOCUMENTS

| | | | |
|---|---|---|---|
| WO | 2005020931 | 3/2005 | |
| WO | WO-2018165731 A1 * | 9/2018 | A61B 18/1485 |

* cited by examiner

DEVICE, SYSTEM AND METHOD FOR TREATING SWOLLEN VASCULAR STRUCTURES

TECHNICAL FIELD

The present invention refers to the treatments of swollen vascular structures by the RF application into said vascular structures and tissues presented in a body canal of a patient. The present invention is situated in the field of medical science, more precisely in treatment of vascular structures, and medical devices.

BACKGROUND TECHNIQUE

There are many different types of diseases related to vascular structures, precisely regarding the swollen or inflammation of said structures. One example of these diseases is the hemorrhoids. Currently, Hemorrhoidal diseases reach a large part of the world population. Some researches show that approximately 50% of world population have some kind of hemorrhoidal disease, where it is common among adults aged 45-65, however the young people and some children are conducive to develop a hemorrhoid disease. A research show that up to 75% of adults in Europe and North America will experience hemorrhoids at some point in their lives (Medical News Today, Aug. 5, 2016). Also, hemorrhoids may be developed in pregnant women.

Basically, hemorrhoids are swollen or inflamed vascular structures in anal canal. It may be caused by excess pressure on these structures, where such structures are composed by blood vessels, and this excess pressure can implies them weaken and fail, allowing blood to flow in wrong direction or to stagnate. Thus, these blood vessels may engorge with blood, resulting in hemorrhoids. Some additional factors as pregnancy, hard faeces and straining may worsen the clinical status with pain and bleeding. After some time the hemorrhoids cushion get greater and greater.

Hemorrhoidal diseases may be found in two types: Internal or External. Internal hemorrhoids develop in anal canal at the level of anorectal line due to enlargement of internal hemorrhoidal venous plexus and the External hemorrhoids is the consequence of enlargement of external hemorrhoidal venous plexus at the anal borders. The prolapsing of hemorrhoids through the anal orifice is thought to be caused by the enlargement of the cushions and a deterioration of the supporting connective tissue under the venous plexus. The connective tissue in the lower rectum may present a degenerative process in the collagen fibers and fibroelastic tissues.

Nowadays, some methods are being used intended to treat hemorrhoids. Common methods suggest the removal of the vascular structures by surgical means, where the patient requires to be sedated and the surgeon makes the incision in the rectal area to reach the vascular structures and then removal it. Usually, this method requires the hospitalization of the patient even after the surgery. Furthermore this method provides a slower recovery for the patient and morbidity represented especially by discomfort and anal pain, once the surgery is made in a sensitive region of the body.

A search in scientific and patent literature pointed relevant documents for the present invention, which is described below.

Document U.S. Pat. No. 7,160,294 B2 discloses a system and method for treating hemorrhoidal disease, where it provides an anoscope comprising a retractable and curve electrode passing through a hole, said electrode configured to apply radiofrequency waves over the rectal artery in order to closing it. However, said document fails to show means for regulation the depth of the electrode, where this lead consequences for reach the artery to be treated. Furthermore, document U.S. Pat. No. 7,160,294 does not certify if the artery is really closed, and if the medical procedure was successfully completed.

Document US 2012/004546 A1 discloses a system and method for treating hemorrhoids where it provides a fiber optic as a laser emitter and an ultrasound probe for detecting the positioning of the artery to be treated. Both elements are introduced in a tube which is inserted in the rectal area of the patient. Two embodiments have been proposed in this solution, where one describes the fiber optic in opposite with the probe, and the other describes the fiber optic facing the probe, however in both embodiments there is a need of additional movement for the using of the device (the one refers to rotational movement, and the other refers to "pull back" movement). Additionally, the fiber optic and the probe must be inserted and positioned manually, where it contributes for medical failures during the procedure.

Document PI 0618702-1 A2 describes a device and method for surgical procedures related to rectal prolapse or hemorrhoids, where it contains an anoscope provided with an aperture in such a way that it allows the surgeon inserting the tools to perform the procedure. In this sense, this solution provides a process regarding the closing of the artery to be treated by means of a suturing thread.

As can be inferred from literature, there are no documents suggesting or anticipating the teachings of the present invention, so that the solution proposed here has novelty and inventive step outside the state of the art.

SUMMARY

The present invention provides device, system and methods for the treatment of swollen vascular structures in a body canal, in order to apply RF (radiofrequency) over the said structures causing a blood flow disruption. The treatment comprises the positioning of the device in the area to be treated, where the positioning is made by an ultrasound probe, and the application of the RF over the vascular structure is performed by a surgical arrangement. Following, the ultrasound probe is responsible to verify whether the vascular structure is disrupted or not.

In an embodiment, the present invention is related to hemorrhoidal diseases, where the treatment comprises the positioning of the device in the rectal area, and detecting the artery to be treated by ultrasound probe. Further, the surgical arrangement is positioned and regulated for the application of RF over the rectal artery to be treated. The treatment includes ultrasound detecting in order to verify whether the rectal artery is already close. Also, the treatment may include the RF emission by surgical arrangement beneath the hemorrhoidal piles in order to promote an inflammatory process in the underlining connective tissue that may retract and positioning upward the hemorrhoidal piles that will shrink after blood supply cut. For such treatment, the treatment device comprises specific equipment for promoting the RF application in the region, and also it comprises triggering equipment and shape adapted to be inserted in the rectal area. The device, system and method were performed for minimizing or annulling the patient's pain or disturb and also facilitating the treatment for the operator.

In an first aspect, the present invention describes a device for treating swollen vascular structures in a body canal, wherein it comprises at least a tubular element (13) adapted to be inserted into body canal comprising at least an ultrasound probe (11) aligned with at least a surgical arrangement (12), wherein the ultrasound probe (11) is fixed at the tubular element (13).

In a second aspect, the present invention provides a system for treating swollen vascular structures in a body canal, wherein it comprises the device (10) for treating swollen vascular structures in a body canal as previously defined; at least a RF source; and at least an ultrasound device; wherein the device (10) is connected with the RF source, and the ultrasound device by plug connectors (17); the RF source provides the RF to the primary RF emitter (12.1) and to the secondary RF emitter (12.2) of the surgical arrangement (12); and the ultrasound device provides the ultrasound signal to the ultrasound probe (11) and processing the signal detected by the probe (11).

In a third aspect, the present invention describes a method for treating swollen vascular structures in a body canal wherein it comprises the steps of: insertion of a tubular element (13) into the body canal of a patient; detection of swollen vascular structure using an ultrasound probe (11); positioning of a surgical arrangement (12) in the swollen vascular structure by means of a trigger element (16); regulation of the surgical arrangement (12) by a regulation mechanism (21); emission of RF over the swollen vascular structure by means of the surgical arrangement (12), causing a blood flow disruption; and verifying with the ultrasound probe (11) whether the vascular structure is disrupted.

In a fourth aspect, the present invention provides a method for treating hemorrhoidal diseases wherein it uses the device as previously defined, and it comprises the steps of: insertion of the tubular element (13) into the rectal area of a patient with hemorrhoidal disease; detection of artery (1) with hemorrhoidal region (1.1) using the ultrasound probe (11); positioning of the surgical arrangement (12) by the trigger element (16) in the artery (1) to be treated, wherein the surgical arrangement (12) is connected to a regulation mechanism (21); emission of RF over the artery (1) with the primary RF emitter (12.1), causing a blood flow disruption; and verifying with the ultrasound probe (11) whether the artery is closed (1.2).

These and other aspects of the invention will be immediately appreciated by the well versed in the art, and for companies with interests in the product segment and will be described in sufficient detail to be reproduced in the following description.

BRIEF DESCRIPTION OF THE DRAWINGS

This invention presents the following drawings in order to define an exemplary embodiment of the proposed device, method and system, however, without limiting the scope of protection.

DETAILED DESCRIPTION

Figure 1:
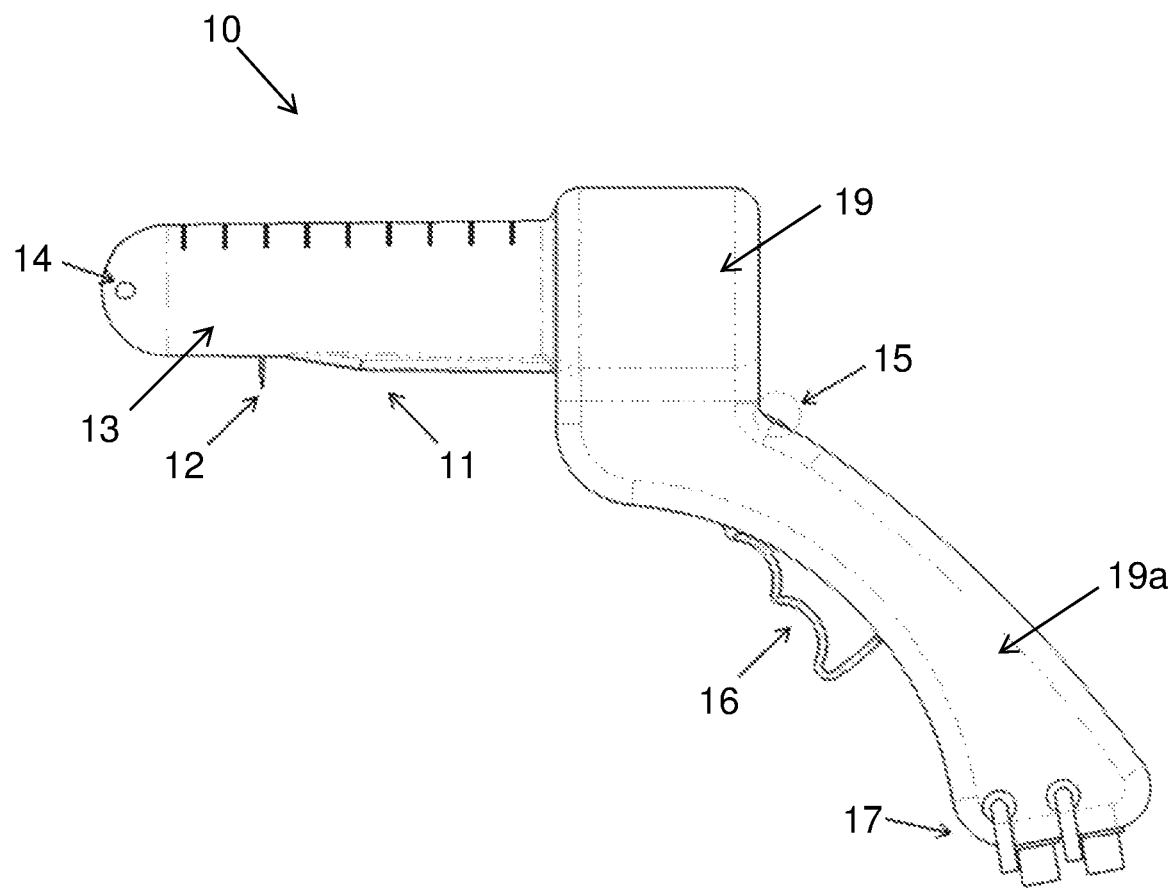
FIG. 1 shows a side view of one embodiment of the device (10) for treating swollen vascular structures.
Figure 2:
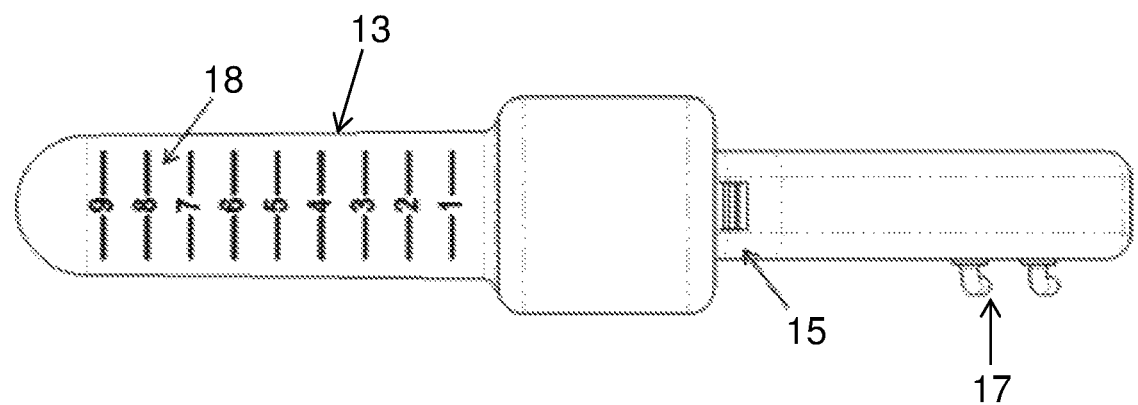
FIG. 2 shows an upper view of one embodiment of the device (10) for treating swollen vascular structures.
Figure 3:
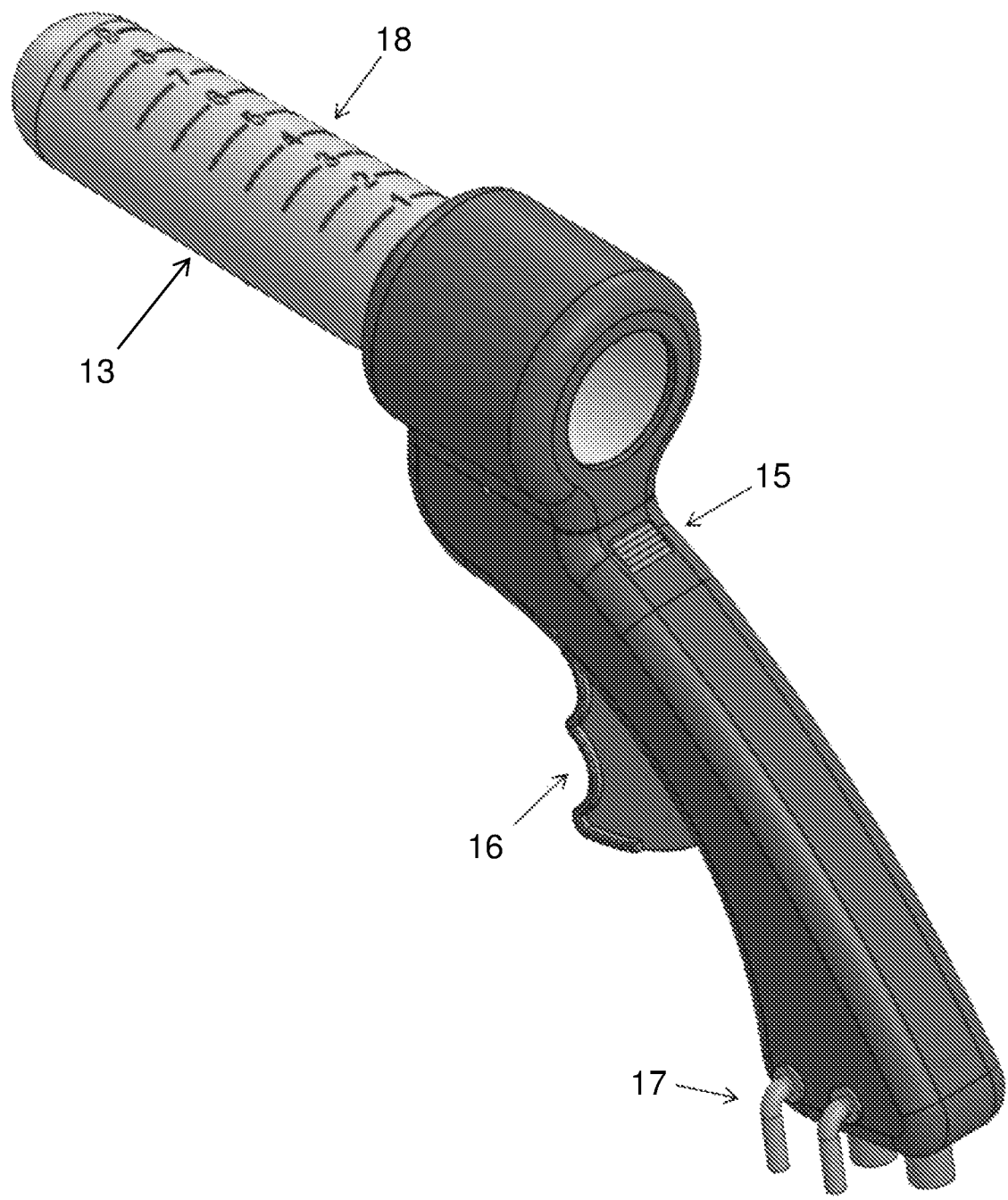
FIG. 3 shows a rear view in perspective of one embodiment of the device (10) for treating swollen vascular structures.
Figure 4:
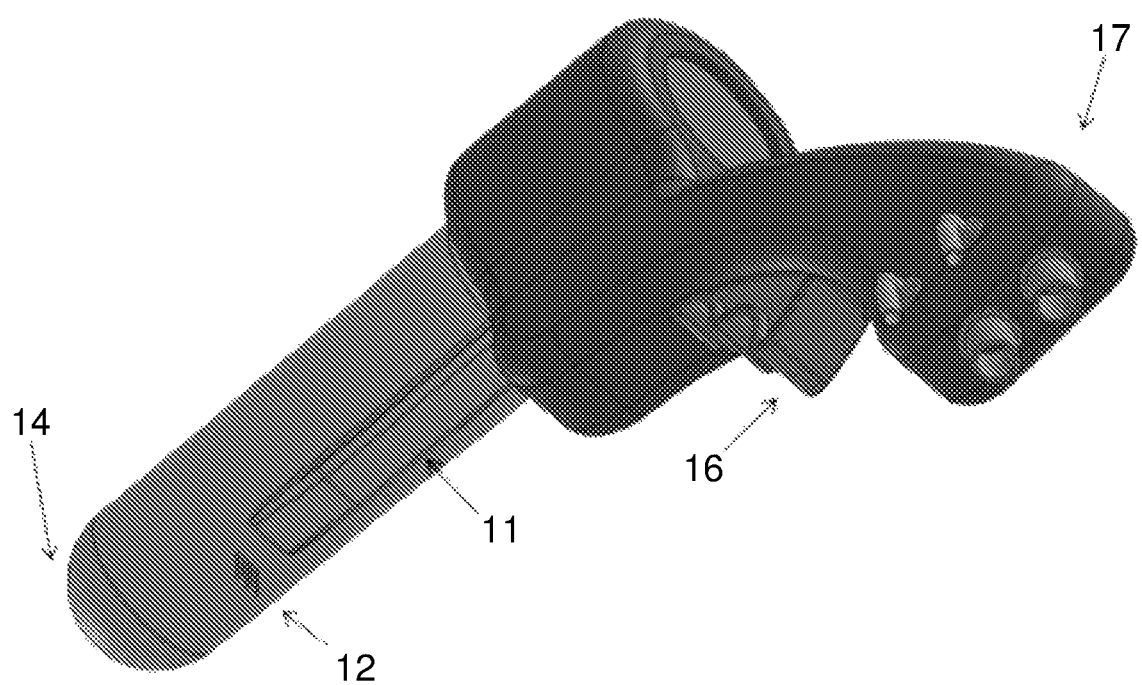
FIG. 4 shows a bottom view in perspective of one embodiment of the device (10) for treating swollen vascular structures.
Figure 5:
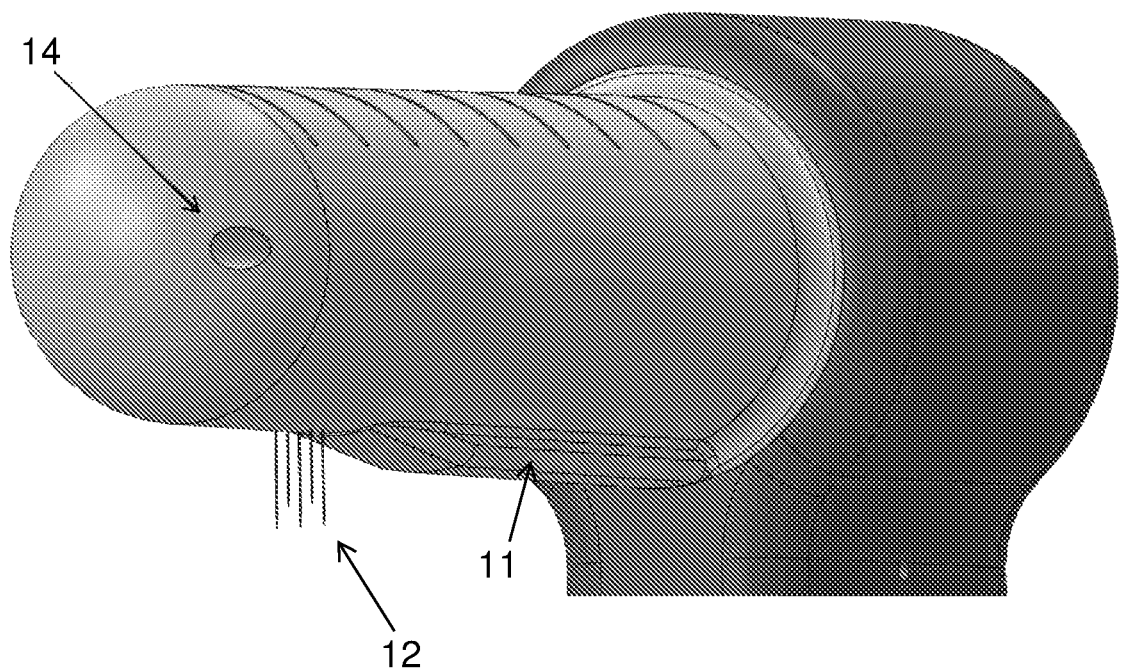
FIG. 5 shows a front view in perspective of one embodiment of the device (10) for treating swollen vascular structures.

The present invention discloses a device, a system and methods for providing treatment for patients that suffer from swollen or inflamed vascular structures present in a body canal. The present invention provides an easy and, practical treatment and with minimal or without disturb to the patient, including RF emission driven directly and specifically over such vascular structure, and by means of ultrasound technology verify the position of the vascular structure and whether it is closed during and after the RF application. Furthermore, the proposed solution provides a simple operation, where it allows that the treatment is performed in a day-clinical center, i.e., the proposed solution does not require a surgical center or surgical procedures to be performed.

The proposed solution has been developed focused on swollen or inflamed vascular structures located in a canal of the patient's body. For example, without limit the scope of the invention, a vascular structure may be understood as a blood vessel, as arteries, veins, arterioles, venules, etc., and a canal may be understood as anal canal, vaginal canal, urinary tract, urethra, nasal canal, etc. Further in such example, a swollen vascular structure located in anal canal is known as hemorrhoids.

In examples regarding hemorrhoids, it is important to highlight that arteries (1), in rectal area, are surrounded by muscles and, therefore, the arteries (1) positioning or depth varies from patient to patient. In view of this point, it is important to have an element to detect the artery (1) both before and during the medical procedure. Also, the arteries (1) depth may vary from patient to patient. Although, this problem is not restricted to hemorrhoidal diseases.

Therefore, in a first aspect, the present invention provides a device for treating swollen vascular structures in a body canal, wherein the device comprises at least a tubular element (13) adapted to be inserted into body canal comprising at least an ultrasound probe (11) aligned with at least a surgical arrangement (12), wherein the ultrasound probe (11) is fixed at the tubular element (13). The alignment of the ultrasound probe (11) with the surgical arrangement (12) allows the monitoring of the vascular structure before, during and after the medical procedure. The alignment may be understood as the ultrasound probe (11) and the surgical arrangement (12) are positioned at the same plane of the tubular element (13). In an embodiment, both the ultrasound probe (11) and the surgical arrangement (12) are positioned in a bottom surface of the tubular element (13). Thus, the ultrasound probe (11) allows that the proposed device (10) operates in closed-loop, since while the RF probes perform the treatment the ultrasound probe (11) provides a feedback to the doctor.

Furthermore, the device (10) comprises at least a base (19) comprising a trigger element (16), wherein the base (19) comprises a connection member geometrically adapted to receive the tubular element (13). Also, the trigger element (16) is associated with at least a lever mechanism (20), where it provides a lever movement when the trigger element (16) is actuated. In an embodiment, the base (19) comprises at least a handhold element (19a), and the trigger element (16) is positioned in such handhold element (19a). Thus, an operator could press the trigger element with the base in the hands, in order to promote a lever movement.

In an embodiment, the lever mechanism is connected to a regulation mechanism (21) by means of at least a linkage element. This connection allows actuation of the regulation mechanism (21) by means of the trigger element (16). For example, without limit the scope of the invention, the linkage element is a beam or a bearing just provided to promote the connection between the lever (20) and the regulation mechanism (21). In an embodiment, the linkage element is located inside the tubular element (13).

Said regulation mechanism (21) is associated with the surgical arrangement (12), in order to provide the regulation of such surgical arrangement (12). This association allows the positioning of the surgical arrangement as needed while the treatment is performed. In an example, the operator of the device (10) is allowed to adjust the depth of the surgical arrangement (12) in order to find the vascular structure inside the patient. Furthermore, in an embodiment, the association between the surgical arrangement (12) and the regulation mechanism (21) is located in the tubular element (13).

In an embodiment, the surgical arrangement (12) comprises a displacement perpendicular to the tubular element (13). This displacement is performed by means of the association between the surgical arrangement (12) and the regulation mechanism (21) as described above. Thus, it is possible to regulate precisely the depth of the surgical arrangement in order to find the vascular structure of the patient to be treated.

Moreover, the surgical arrangement (12) comprises at least a primary RF emitter (12.1) and at least a secondary RF emitter (12.2), where both are RF probes. Said primary RF emitter (12.1) and secondary RF emitter (12.2) are able to be used for the same or different functions. In this sense, both can operate in same frequency or different frequency. In an embodiment, the primary RF emitter (12.1) is longer than the secondary RF emitter (12.2).

In another aspect, the present invention discloses a system for treating swollen vascular structures in a body canal which comprises the device (10) as described before, at least one energy source, at least one RF source, at least one ultrasound device.

The device (10) is connected with the energy source, the RF source, and the ultrasound device by the plug connectors (17).

The RF source provides the RF to the surgical arrangement (12), where the RF waves are led to the probes by means of conductive wire. In an embodiment, the RF source may be a functions generator, which allows the adjustment of the frequency to a desirable value. In an embodiment, the RF source provides RF waves to the primary RF emitter (12.1) and to the secondary RF emitter (12.2).

In an embodiment, the ultrasound device is able to generate an ultrasound signal to the ultrasound probe (11) and processing the signal detected by the probe (11), once ultrasound detections work with reflection waves.

In an embodiment, the system comprises a water source that is associated with the device (10) by means of the plug connectors (17) and allows the cleaning of the area to be treated before the treatment appliance.

In another aspect, the present invention discloses a method for treating swollen vascular structures in a body canal, wherein said method comprises the at least the following steps: insertion of a tubular element (13) into the body canal of a patient; detection of swollen vascular structure using an ultrasound probe (11); positioning of a surgical arrangement (12) in the swollen vascular structure by means of a trigger element (16); regulation of the surgical arrangement (12) by a regulation mechanism (21); emission of RF over the swollen vascular structure by means of the surgical arrangement (12), causing a blood flow disruption; and verifying with the ultrasound probe (11) whether the vascular structure is disrupted.

The said method is performed with the aid of the device (10) as previously defined. In this sense, this allows the treatment of any kinds of diseases related to swollen or inflamed vascular structures located in a canal of the patient's body.

Example

In this example, the present invention is focused on treatment for hemorrhoidal diseases, since hemorrhoids can be quickly explained as swollen or inflamed arteries or arterioles located into the anal canal of a patient.

Therefore, by means of present invention, the treatment is based on radiofrequency applications in the hemorrhoidal arteries and inflamed underlying tissues that implies in hemorrhoidal diseases. The RF application causes a little and controlled damage in the hemorrhoidal region (1.1) producing a blood flow disruption, where this disruption causes a shrink of the artery (1). The RF is applied by means of a probe that is inserted in the artery (1), or positioned near of the artery (1), and it emits an electromagnetic wave in a specified frequency. This specified frequency is known by a person skilled in the art and it is commonly used in medical procedures regarding to blood vessels and vascular structures.

Thus, in view of the pointed out above, it is presented a device as seen in FIG. 1, which refers to a device (10) for treating vascular structures as hemorrhoids diseases, which comprises at least a base (19), which comprises a handhold element (19a), wherein the base (19) comprises an indicator element (15) and a trigger element (16) both positioned at handhold element (19a); and at least a tubular element (13) comprising at least an ultrasound probe (11) aligned with at least a surgical arrangement (12), wherein an illumination device (14) is positioned in a frontal region of the tubular element (13) and a metric scale (18) is positioned in a top surface of the tubular element (13). Wherein, the base (19) comprises a connection member geometrically adapted to receive the tubular element (13).

The insertion of the device (10) in the patient is facilitated by a geometrically adapted shape by comprising the tubular element (13) with an illumination device (14) associated with the base (19) composed with a metric scale (18). Thus, the operator can control the insertion depth by checking the metric scale (18) and the insertion directions with the illumination device (14). In some embodiments, the illumination device (14) is a LED or any other light source that helps the operator in the device insertion.

In an embodiment, the base (19) is associated with the tubular element (13) in a non-permanent association, for example screw or fitting, allowing the separation of the elements for appropriate cleaning or sterilization.

The device (10) further presents the handhold element (19a) with a trigger element (16) and an indicator element (15) for facilitating the RF application. Thus, the trigger element (16) is associated with the indicator element (15) so that when the trigger element (16) is displaced the indicator element (15) is also moved. In an embodiment, this association is made by a set of gears.

Figure 7:
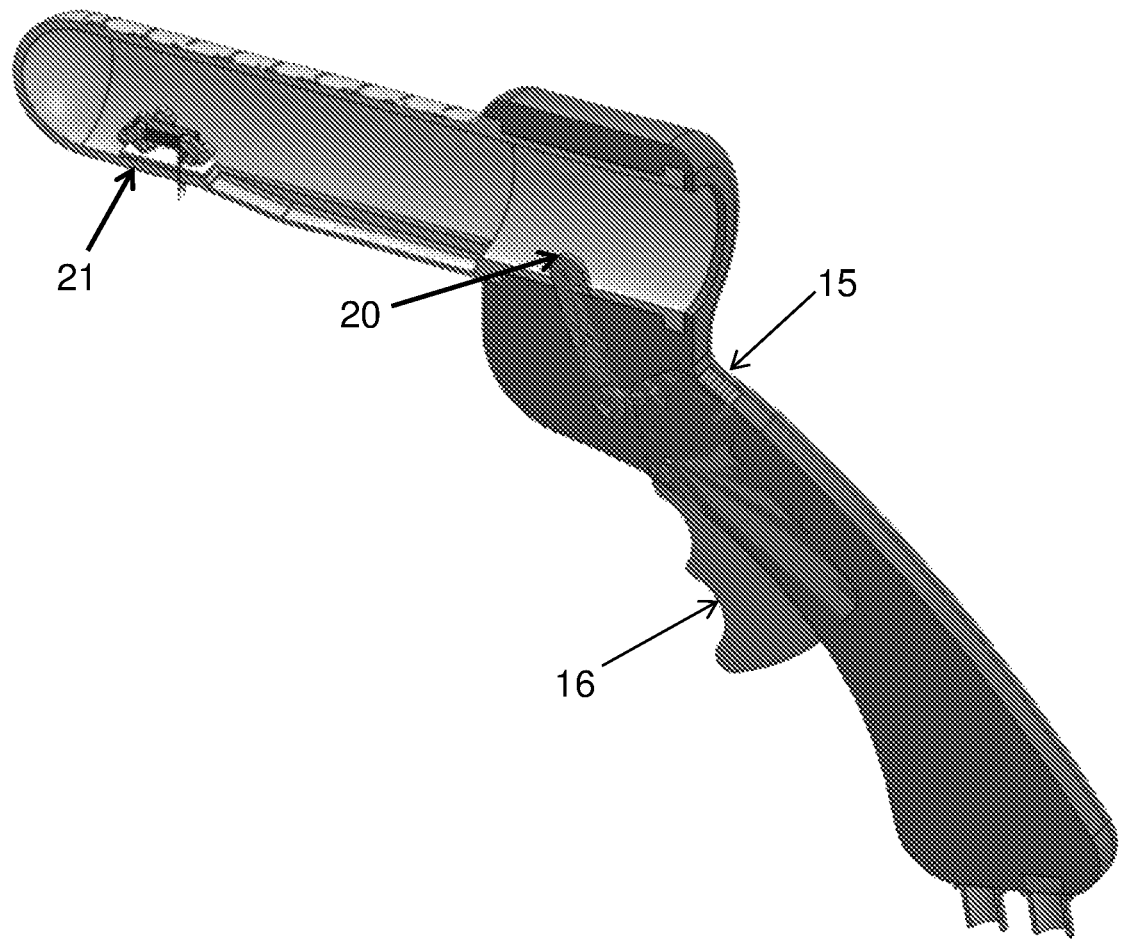
FIG. 7 shows a cross-sectional view of the device (10) for treating swollen vascular structures.

As illustrated by FIG. 7, the trigger element (16) is also associated with a lever mechanism (20), where said lever mechanism (20) is associated with a regulation mechanism (21) by means of at least one linkage element. Thus, the operation of the trigger element (16) provides a changing of the indicator element (15) and a movement of the lever mechanism (20), and thereby the regulation mechanism (21) is actuated by the lever mechanism (20).

Figure 8:
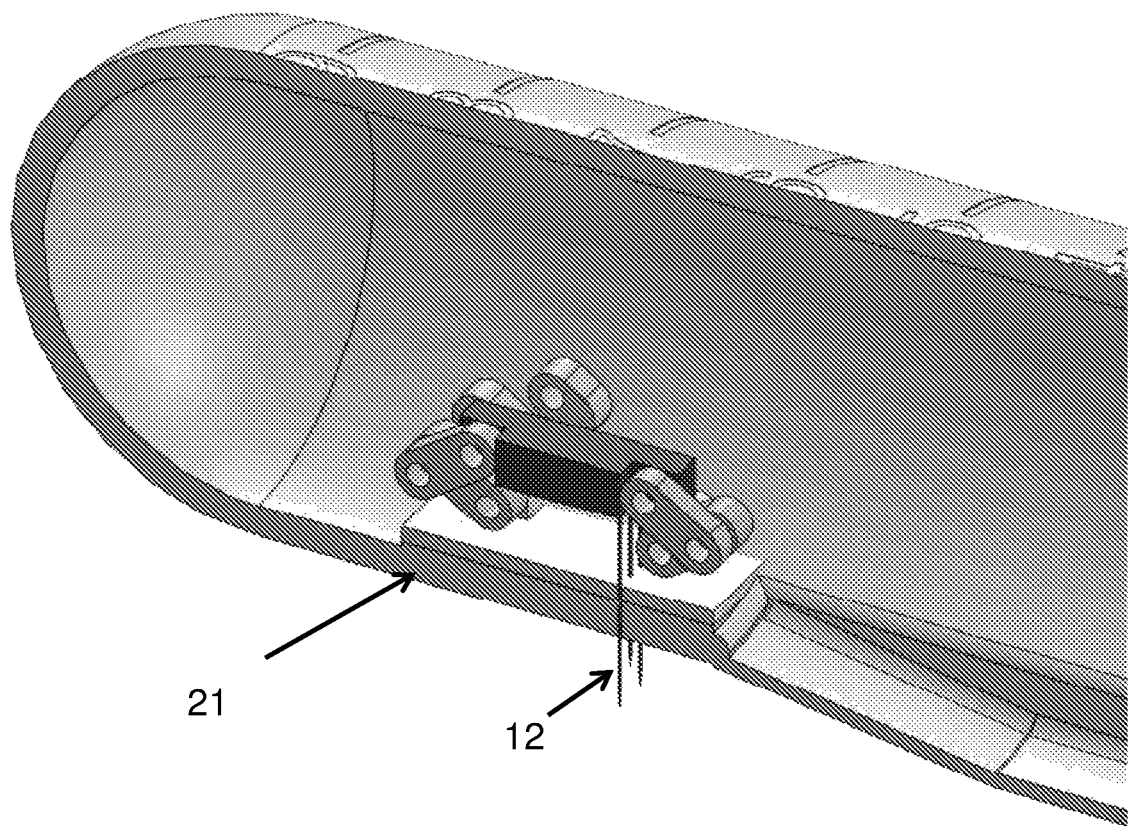
FIG. 8 shows a cross-sectional close-up view of the regulation mechanism (20) of the device (10) for treating swollen vascular structures.
Figure 9:
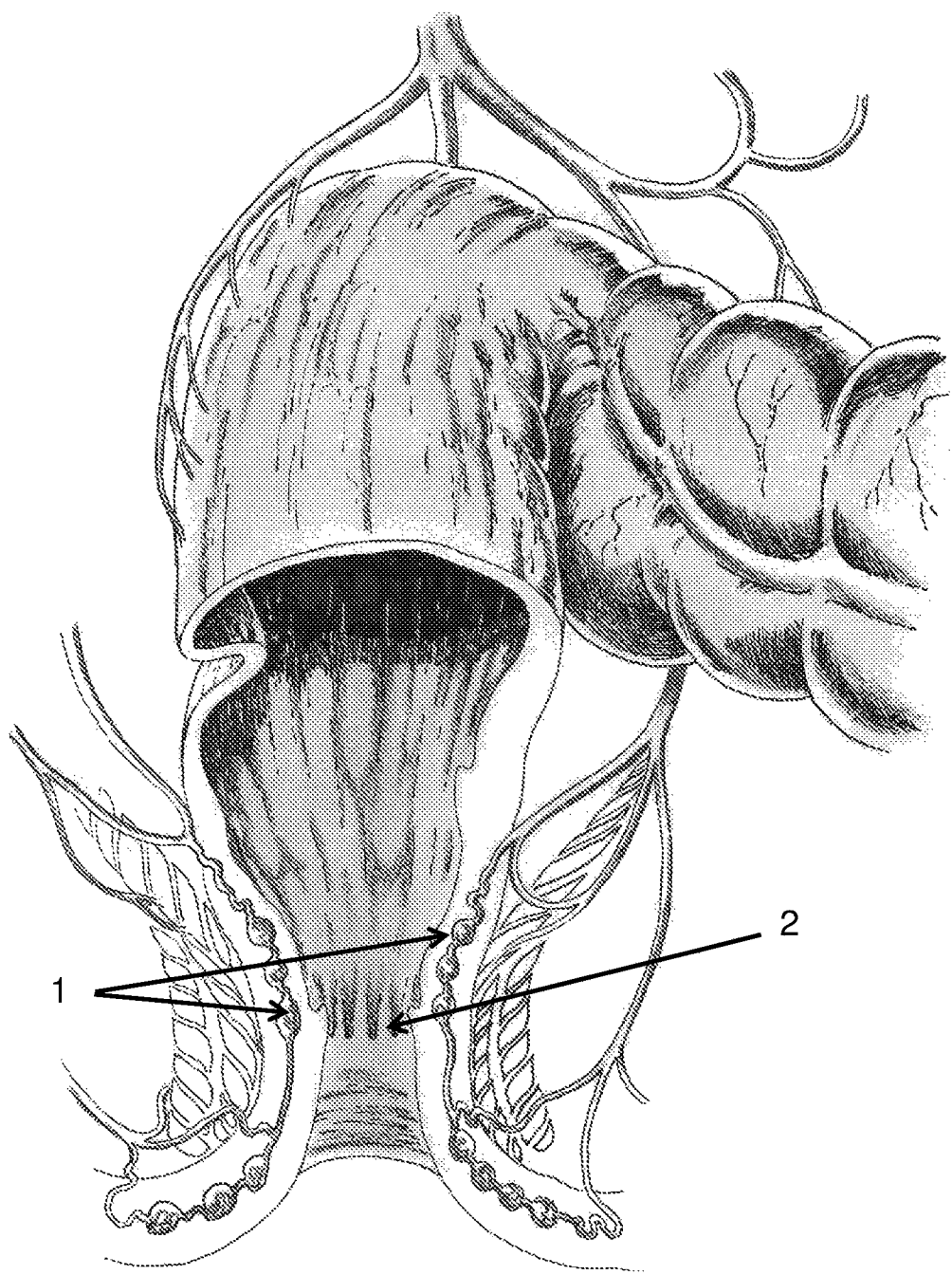
FIG. 9 shows a cross-sectional view of a rectal area indicating the pectinate or dentate line (2) and the arteries (1) of the rectal area.
Figure 10:
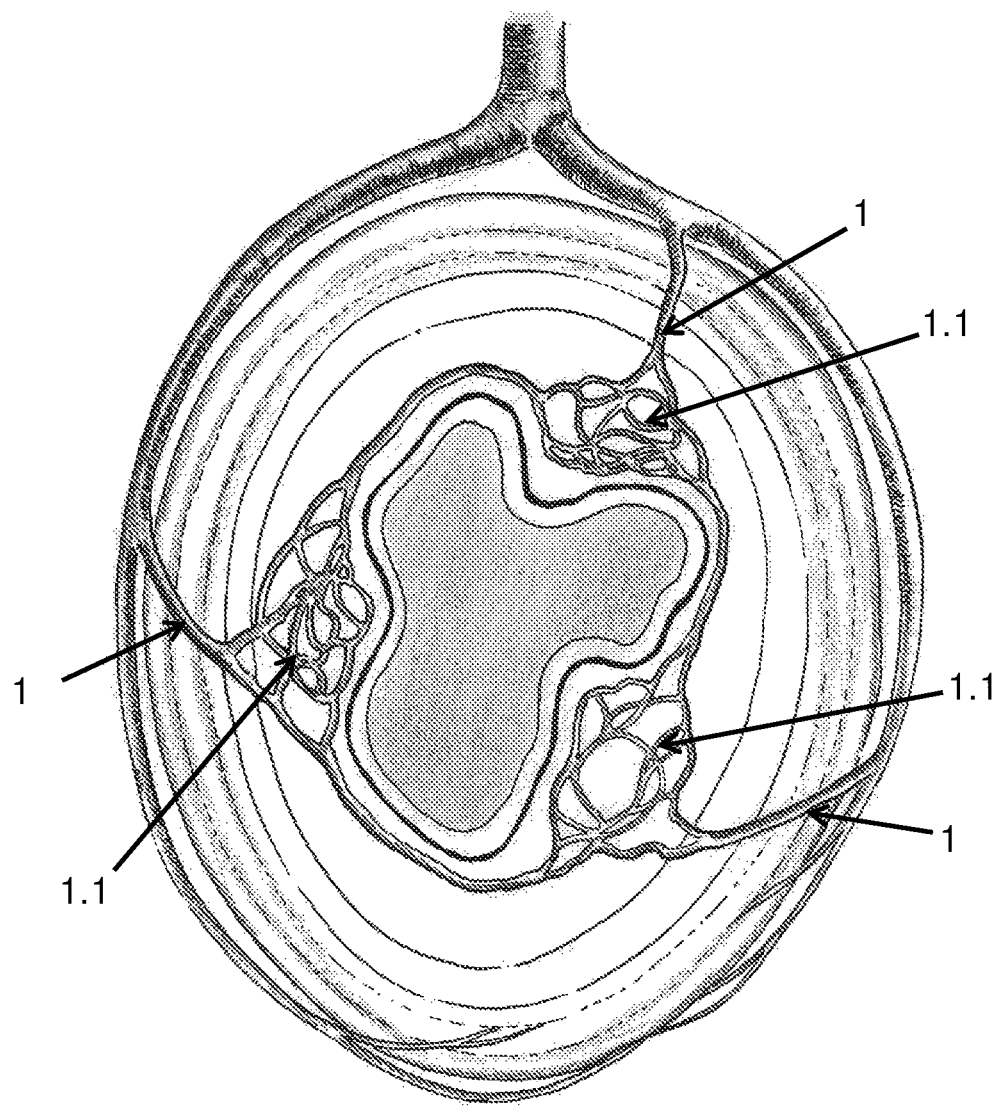
FIG. 10 shows a cross-section upper view of the rectal area, where the three main arteries (1) of the rectal area are detailed along with the hemorrhoidal plexus represented by the hemorrhoidal region (1.1) of the artery (1).
Figure 11:
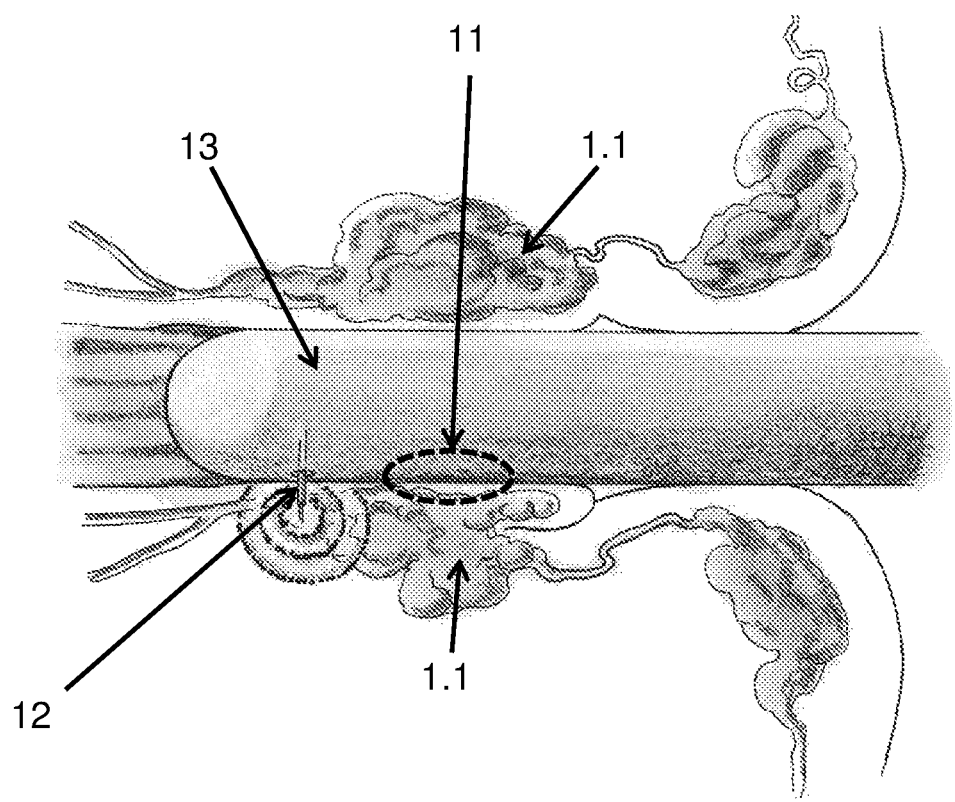
FIG. 11 shows the RF application by the surgical arrangement (12) into a hemorrhoidal region (1.1) after the insertion of the tubular element (13) into the rectal area of a patient.
Figure 12:
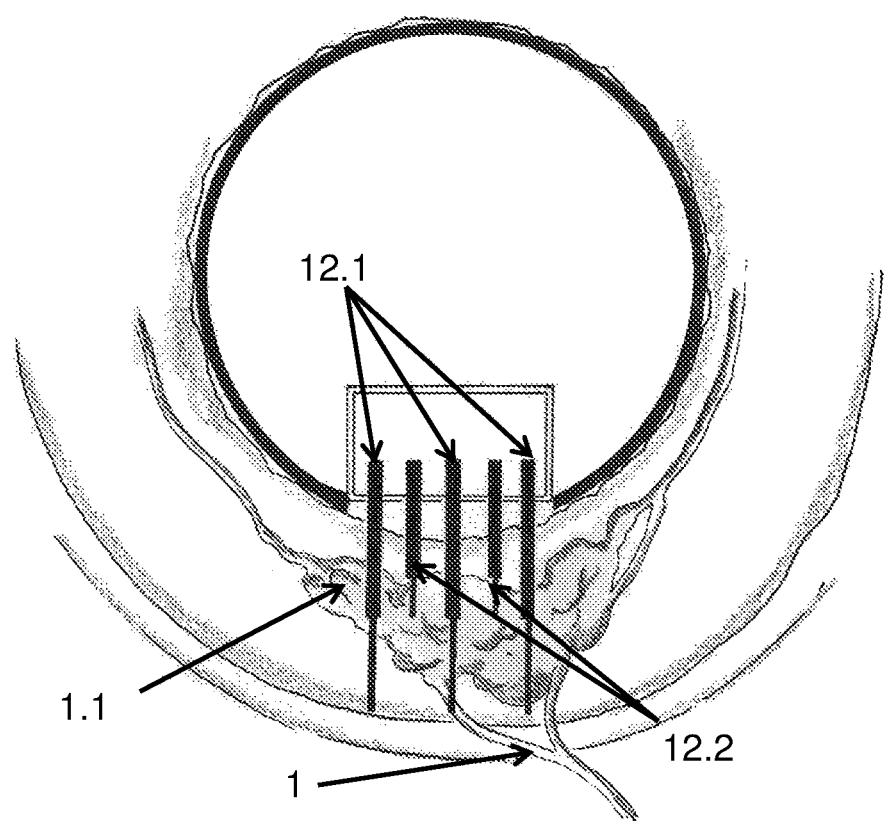
FIG. 12 shows the positioning of the surgical arrangement (12) by the trigger element (16) to the hemorrhoidal region (1.1) to be treated, being the primary RF emitter (12.1) positioned over or above the artery (1) and the secondary RF emitter positioned (12.2) into the connective tissue of the hemorrhoidal region (1.1) underlying the prolapsed rectal mucosa of the lower rectum.
Figure 13:
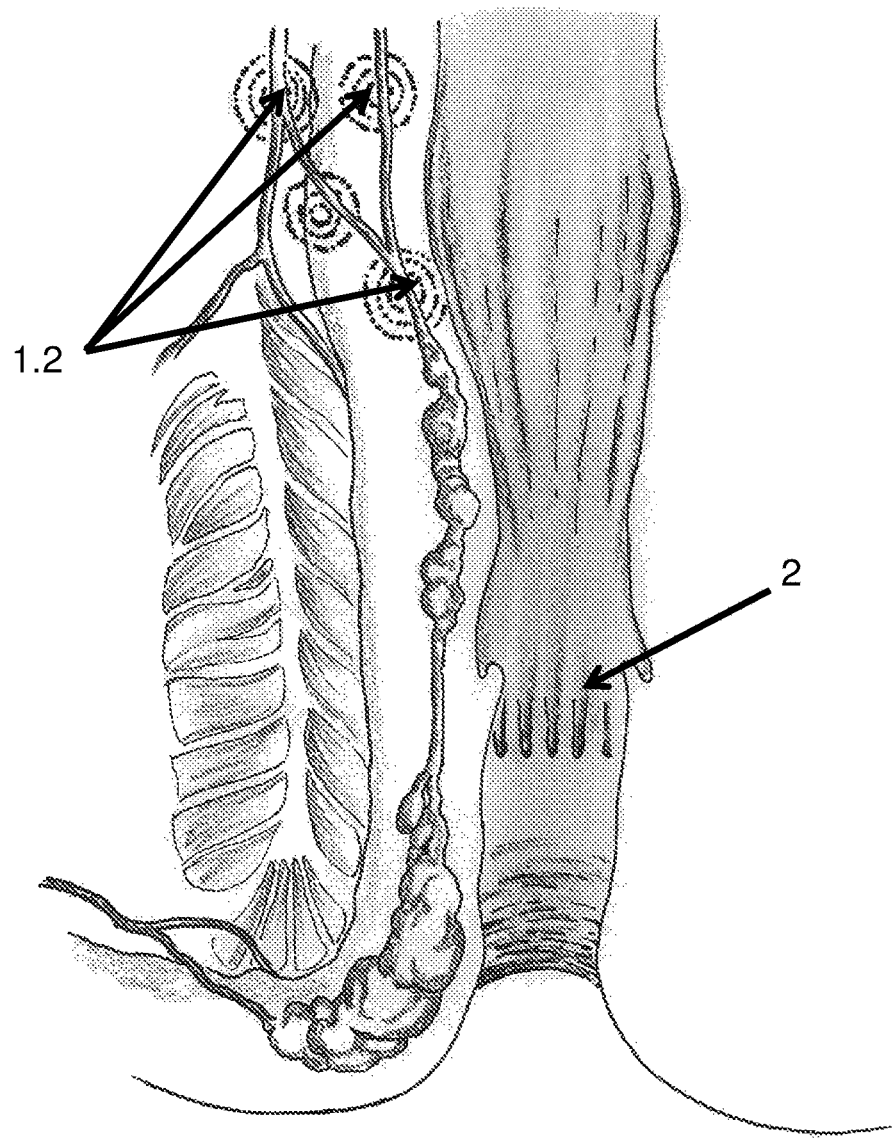
FIG. 13 shows the closure of the arteries (1.2) after the RF emission.
Figure 14:
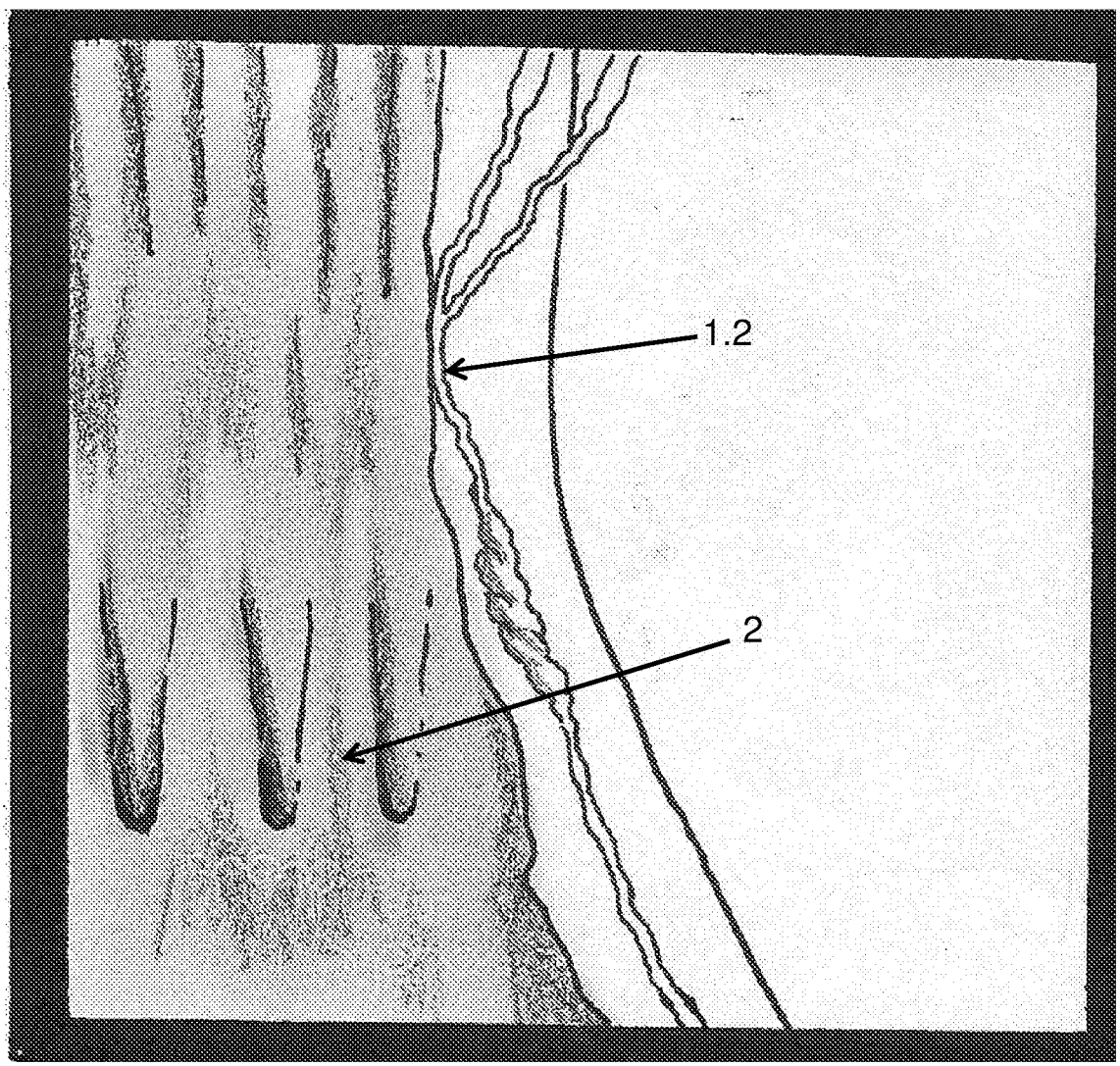
FIG. 14 shows a close-up view of the closed artery (1.2) after the treatment bonded to the rectal wall.

In turn, the regulation mechanism (21) is associated with the surgical arrangement (12), as detailed by FIG. 8. And thus, due the associations described above and shown in the figures, the trigger element (16) can control the surgical arrangement (12) position. Therefore, in an embodiment, the operator checks the surgical arrangement (12) position in the indicator element (15) and adjusts the positioning by operating the trigger element (16).

In an embodiment, the surgical arrangement (12) is composed by RF probes and it is located at a bottom surface of the tubular element (13). Further, the surgical arrangement (12) comprises a displacement perpendicular to the tubular element (13), i.e., it can perform a displacement both to outwardly and inwardly of the tubular element (13). In another embodiment, the surgical arrangement (12) is composed by RF probes performing an angular displacement in relation to the tubular element (13).

As previously mentioned, the depth of the artery (1) may vary in some patients, thus, the displacement performed by the surgical arrangement (12) allows the depth regulation of the RF probes, where it is possible due to regulation mechanism (21). Therefore, the association between the trigger element (16), the lever mechanism (20) and the regulation mechanism (21) defines the depth control of the surgical arrangement (12). Thus, in the operation of the device (10), an operator can control how deep the probes of the surgical arrangement (12) are inserted or neared of the vascular structures of the patient. This procedure is performed to ensure that the probes are introduced just over or very close to the artery (1). In an embodiment, the surgical arrangement (12) can reach a depth of 3 to 13 millimeters.

The surgical arrangement (12) comprises at least one primary RF emitter (12.1) and at least one secondary RF emitter (12.2), where both are RF probes. The primary RF emitters (12.1) is used for the application of the RF just over or very close to the artery (1) to be treated, and thus for disrupts the blood flow. The secondary primary RF emitter (12.2) is used for binding the connective tissue of the hemorrhoidal region (1.1) underlying the prolapsed rectal mucosa of the lower rectum, where this RF application is made in the deteriorate supporting tissues of the hemorrhoidal region (1.1). Thus, this device (10) is used for the ligature of the hemorrhoidal region (1.1) and the pexia of the displaced connective of the inferior rectal wall and anal canal.

Figure 6:
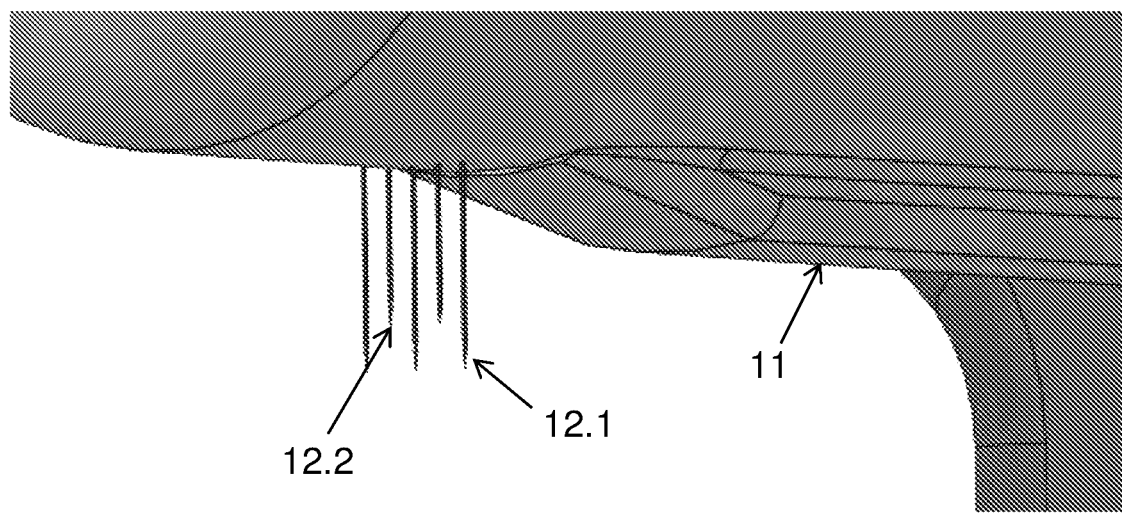
FIG. 6 shows a close-up view of the surgical arrangement (12) of the device (10) for treating swollen vascular structures.

FIG. 6 illustrates an embodiment in which the surgical arrangement (12) comprises three primary RF emitters (12.1) and two secondary RF emitters (12.2). In an embodiment, the primary RF emitter (12.1) comprises a length longer than the secondary RF emitter (12.2), where this arrangement allows that the primary RF emitter (12.1) reaches the artery (1), and the secondary RF emitter (12.2) reaches the surrounding connective tissue of the hemorrhoidal region (1.1), fixing them to the rectal wall.

In an embodiment, the trigger element (16) allow the control of the primary (12.1) and secondary (12.2) RF emitters independently or concurrently. Also, the indicator element (15) indicates the positioning of the RF emitters independently or concurrently.

Further, the ultrasound probe (11) is positioned in the device (10) aligned with the surgical arrangement (12), also in the bottom surface of the tubular element (13). The ultrasound probe (11) is used to detect the artery (1) to be treated sensing it by means of its pulsation caused by blood flow. The ultrasound probe (11) remains on during the entire procedure, in order to verify if the artery (1) involved in the treatment is closed or if it still opened, i.e., if the ultrasound probe (11) does sense the pulsation it indicates that the artery (1) is still opened, on the other hand, if the ultrasound probe (11) does not sense the pulsation, the artery is closed (1.2). Therefore, the operator is advised if the procedure is adequate to be finished or if the procedure must be continued.

The device (10) also includes plug connectors (17) in the base (19) for association with external resource such as energy resources, water resources, ultrasound source, RF source, and light sources.

In another aspect, present invention discloses a method for treating hemorrhoidal diseases, using the device described above, which comprises the steps of: insertion of the tubular element (13) into the rectal area of a patient with hemorrhoidal disease; detection of the artery (1) with the hemorrhoidal region (1.1) (or hemorrhoidal plexus) by means of the ultrasound probe (11); positioning of the surgical arrangement (12) by the trigger element (16) in the artery (1) to be treated, wherein the surgical arrangement (12) is connected to a regulation mechanism (21); emission of RF over the artery (1) with the primary RF emitter (12.1), causing a blood flow disruption; verifying with the ultrasound probe (11) whether the artery is closed (1.2).

Initially, an operator inserts the tubular element (13) in the rectal area of the patient, where this step is facilitated with the geometry of the tubular element (13) and with the metric scale (18) for verifying how the tubular element (13) must be inserted in the patient for the RF appliance. Then, the operator initiates the detection procedure of the hemorrhoidal region (1.1) of the artery (1) by means of the ultrasound probe (11), rotating the device (10) until the artery (1) is detected.

Thus, the operator positions the surgical arrangement (12) in the area to be treated, where this step is made by the trigger element (16) and facilitated with the indicator element (15) that indicates the depth of the surgical arrangement (12).

Additionally, after the positioning of the surgical arrangement (12) in the area, the operator adjusts the depth of the surgical arrangement (12) until the same reaches the desirable region. Thus, the depth reached by the surgical arrangement (12) is defined accordingly the depth of the artery (1) in the rectal area of the patient with hemorrhoidal disease. Thus, when the primary RF emitter (12.1) reaches the patient's artery (1) with hemorrhoidal region (1.1) (or hemorrhoidal plexus), the operator may initiate the next step.

After the proper positioning, the primary RF emitter (12.1) is inserted in the artery (1), or positioned close to the artery (1), and it emits the RF into the rectal artery (1). Such process is verified by the ultrasound probe (11), which detects the pulsation of the artery (1) before, during and after the procedure. Thus, since the ultrasound probe (11) does not detecting the pulse of the artery (1), the blood flow is already disrupted.

In an embodiment, the surgical arrangement (12) is positioned above the pectinate or dentate line (2), and thus it provides a painless or without discomfort hemorrhoidal diseases treatment for the patient.

Further, to complement and improve the treatment, the present method provides a step of RF application in the hemorrhoidal region (1.1) of the artery (1), by means of the secondary RF emitter (12.2). The rectal artery treatment may result in some prominent skin area or tissue due to hemorrhoidal region (1.1), thus this step of emission of RF with the secondary RF emitter (12.2) allows the pexia of prominent skin or tissues caused by hemorrhoidal region (1.1), where they are fixed to the rectal wall avoiding post-surgical complications for the patients.

In an embodiment, the RF application in hemorrhoidal region (1.1) to bind connective tissue of the hemorrhoidal region (1.1) underlying the prolapsed rectal mucosa of the lower rectum in rectal wall occurs simultaneously to the RF application into the artery (1). In another embodiment, the RF application in hemorrhoidal region (1.1) to bind connective tissue underlying the prolapsed rectal mucosa of the lower rectum related to said hemorrhoidal region (1.1) in rectal wall occurs independently to the RF application into the artery (1).

Therefore, this example of the invention promotes a safe, practical and precise treatment for hemorrhoids diseases, painless and with minimal discomfort for the patient and facilitating the process for the operator. Finally, the proposed device, system and method were developed to ensure an effective treatment in cases of hemorrhoidal diseases, where the present solution provides the ligature of the hemorrhoidal artery and possible replacement of to normal position of tissues in the rectal wall, by means of radiofrequency application by at least two probes (or two set of probes) operating in distinct areas, and an ultrasound probe (11) to detect whether the artery (1) is closed, sensing its pulsation.

Those well versed in the art will value the knowledge here, and may reproduce the invention in the manner provided and other variants, covered within the scope of appended claims.

The invention claimed is:

1. A device for treating swollen vascular structures in a body canal characterized in that it comprises at least a tubular element (13) adapted to be inserted into body canal comprising at least an ultrasound probe (11) aligned with at least a surgical arrangement (12) comprising a primary RF emitter (12.1) adapted to extend a dissimilar length from the surgical arrangement (12) than a secondary RF emitter (12.2) is adapted to extend from the surgical arrangement (12), wherein the ultrasound probe (11) is fixed at the tubular element (13) to verify if an artery (1) with a hemorrhoidal region (1.1) involved in treating swollen vascular structures in a body canal is closed or if the artery (1) is open;

wherein, the primary RF emitter (12.1) is configured to extend to reach the artery (1) with a hemorrhoidal region (1.1), and the secondary RF emitter (12.2) is configured to extend to reach a surrounding connective tissue of the hemorrhoidal region (1.1) underlying the prolapsed rectal mucosa of the lower rectum; and wherein the secondary RF emitter (12.2) delivers RF for binding the said surrounding connective tissue of the hemorrhoidal region.

2. The device according to claim 1 characterized in that it further comprises at a least a base (19) comprising a trigger element (16), wherein the base (19) comprises a connection member geometrically adapted to receive the tubular element (13).

3. The device according to claim 2 characterized in that it further comprises a lever mechanism (20) associated with the trigger element (16).

4. The device according to claim 1 characterized in that the tubular element (13) comprises at least a regulation mechanism (21) associated with the surgical arrangement (12).

5. The device according to claim 4 characterized in that the lever mechanism (20) is connected to the regulation mechanism (21) by means of at least a linkage element.

6. A system for treating swollen vascular structures in a body canal characterized in that it comprises:
   a. a device (10) for treating swollen vascular structures in a body canal as defined in claim 1;
   b. at least a RF source; and
   c. at least an ultrasound device;
wherein,
   the device (10) is connected with the RF source, and the ultrasound device by plug connectors (17);
   the RF source provides the RF to the primary RF emitter (12.1) and to the secondary RF emitter (12.2) of the surgical arrangement (12); and
   the ultrasound device provides the ultrasound signal to the ultrasound probe (11) and processing the signal detected by the probe (11) to determine pulsation of an artery (1) and to verify if the artery (1) is closed or open.

7. The device according to claim 1 characterized in that it further comprises at least a handhold element (19a) comprising a trigger element (16) associated with an indicator element (15), wherein the position of the surgical arrangement (12) is checkable in the indicator element (15) and adjustable by the trigger element (16).

8. The device according to claim 1 characterized in that the primary RF emitter (12.1) comprises a plurality of primary RF probes, and the secondary RF emitter (12.2) comprises a plurality of secondary RF probes, and wherein the plurality of primary RF probes and the plurality of secondary RF probes are arranged in parallel and intercalated to each other.

9. The device according to claim 1 characterized in that the primary RF emitter (12.1) comprises a plurality of primary RF probes, and the secondary RF emitter (12.2) comprises a plurality of secondary RF probes, and wherein the plurality of primary RF probes and the plurality of secondary RF probes are interlaced and spaced among each other to extend from a single line that is perpendicular to a central radial axis of the tubular element (13).

\* \* \* \* \*